United States Patent [19]

Alfano

[11] Patent Number: 4,581,015
[45] Date of Patent: Apr. 8, 1986

[54] MULTIMEDICATION SYRINGE

[76] Inventor: C. Michael Alfano, 439 Richland Blvd., Brightwaters, N.Y. 11718

[21] Appl. No.: 608,884

[22] Filed: May 10, 1984

[51] Int. Cl.$^4$ .............................................. A61M 5/22
[52] U.S. Cl. ................................... 604/88; 604/56; 604/232; 604/244
[58] Field of Search .................... 604/88, 232, 82, 56, 604/86, 218, 244

[56] References Cited

U.S. PATENT DOCUMENTS

| | | | |
|---|---|---|---|
| 2,346,334 | 4/1944 | Shaw | 604/86 |
| 3,470,874 | 10/1969 | Accetta | 604/88 |
| 3,489,147 | 1/1970 | Shaw | 604/88 |
| 3,566,868 | 3/1971 | Baptist | 604/56 |
| 3,659,749 | 5/1972 | Schwartz | 222/145 |
| 4,005,710 | 2/1977 | Zeddies et al. | 128/214 R |
| 4,076,023 | 2/1978 | Martinez | 128/214 R |
| 4,121,585 | 10/1978 | Becker, Jr. | 128/214 R |
| 4,165,742 | 8/1979 | Gardner | 128/229 |
| 4,197,848 | 4/1980 | Garrett et al. | 128/247 |
| 4,204,525 | 5/1980 | Olson | 128/1 R |
| 4,294,249 | 10/1981 | Sheehan et al. | 128/214 G |
| 4,392,851 | 7/1983 | Elias | 604/82 |
| 4,465,471 | 8/1984 | Harris et al. | 604/92 |
| 4,471,765 | 9/1984 | Strauss et al. | 604/232 |
| 4,472,141 | 9/1984 | Dragan | 604/232 |

Primary Examiner—Andrew H. Metz
Assistant Examiner—Anthony McFarlane
Attorney, Agent, or Firm—Finnegan, Henderson, Farabow, Garrett & Dunner

[57] ABSTRACT

A multimedication syringe for temporary storage and injection of at least two fluid substances comprising a hollow tubular housing having a generally cylindrical wall, an open rear end and a generally tapered partially closed front end defining a discharge passage; a plunger including a portion sized for moving axially within the housing through substantially the entire length thereof, the portion including a plug surrounding the portion for engaging the inner surface of the housing in a fluid-tight manner, the plunger for forcing fluid in the housing out the discharge passage when the plunger is moved axially within the housing from the open end toward the discharge passage; and a resealable tube in the wall of the housing for transmitting fluid into the housing.

8 Claims, 3 Drawing Figures

MULTIMEDICATION SYRINGE

FIELD OF THE INVENTION

This invention relates to the field of medicine, and more particularly to syringes and methods for administering medicines by the use of syringes.

BACKGROUND OF THE INVENTION

Syringes are well known in the medical and surgical field, and have been used for many years for injecting drugs and other substances into patients. Such medications are available in multidose vials and single dose vials. However, because of cost considerations, the multidose vial is much more economical. If a patient is only receiving a single medication in a given injection, the use of a multiple-dose vial does not create problems, since a sterile syringe can be used to draw the necessary medication from the vial without contamination of the remaining medication. However, in situations where a patient is to receive multiple medications in a single injection, the use of multiple-dose vials becomes a problem. If a first medication is drawn into a syringe from a multiple dose vial, insertion of this syringe into a second such vial will contaminate the second vial with some of the first medication, or with other foreign substances. As a result, the use of multiple-dose vials has decreased substantially in the last several years, in favor of single-dose vials. This leads to an increase in expense to the patient, & practitioner, & institution as well as inefficient and uneconomical use of resources.

Despite the above problems, nothing appears to be available in the prior art which is capable of alleviating these problems. While syringes for storing and intermixing various ingredients are well known, none of these syringes are capable of receiving multiple medications from multiple-dose vials without contaminating at least one of the vials. For example, Schwartz U.S. Pat. No. 3,659,749 describes an intermixing syringe including means for isolating the storage of two components prior to their being mixed. In the disclosed invention, two isolated portions are provided within the syringe for receiving separate medicines. However, there is no suggestion of providing a separate port for injecting multiple medicines into the syringe itself.

Although resealable puncturable membranes have been utilized in the medical field previously, applicant is unaware of any use of such a membrane for sealing an auxiliary port in a syringe. Sheehan et al., U.S. Pat. No. 4,294,249 describes a swage-molded injection site which includes a self-sealing puncturable member of resilient material and a housing wherein the puncturable member is compressably confined. The injection site is designed for attachment to an intravenous assembly, but there is no suggestion of using such a member for sealing an auxiliary port in a syringe.

Accordingly, it is a primary object of this invention to increase the use of multiple-dose vials of medicines.

It is a further object of this invention to allow multiple medications to be injected in a single injection without contamination of the supply of such medications.

Yet another object of the invention is to economically provide a multimedication syringe which is simple to operate.

A still further object of the invention is to prevent contamination of multiple-dose vials while allowing multimedication injections.

Additional objects and advantages will be set forth in part in the description which follows, and in part, will be obvious from the description, or may be learned by practice of the invention.

SUMMARY OF THE INVENTION

To achieve the foregoing objects and in accordance with the purpose of the invention, as embodied and broadly described herein, the multimedication syringe of the present invention is for temporary storage and injection of at least two fluid substances. The syringe comprises a hollow tubular housing having a generally cylindrical wall, an open rear end and a generally tapered partially closed front end defining a discharge passage; a plunger including a portion sized for moving axially within the housing through substantially the entire length thereof, the portion including sealing means surrounding the portion for engaging the inner surface of the housing in a fluid-tight manner, the plunger for forcing fluid in the housing out the discharge passage when the plunger is moved axially within the housing from the open end toward the discharge passage; and resealable port means in the wall of the housing for transmitting fluid into the housing.

Preferably, the syringe also includes removable means for sealing the discharge passage. The port means preferably includes a tube having a resilient self-sealing membrane therein, the tube being mounted to the housing for allowing insertion of a syringe needle through the membrane.

It is also preferred that the plunger include a flattened end for manually depressing the plunger, and that the sealing means include a cylindrical plug having ridges thereon for engaging the inner surface of the housing.

The tube is preferably positioned on the housing for allowing the plug to seal the open end of the housing without interference with the fluid transmission through the tube.

The invention also includes a method of administering multimedicines in a single dose without contamination of the supplies of the medicines. The method comprises the steps of drawing a first medicine into a first syringe from a supply thereof through the discharge passage of the first syringe; drawing a second medicine from a supply thereof into a second syringe through the discharge passage thereof; injecting the second medicine into the first syringe through a port in the wall of the first syringe; and injecting the multiple medicines into a patient through the discharge passage of the first syringe.

BRIEF DESCRIPTION OF THE DRAWINGS

The accompanying drawings which are incorporated in and constitute a part of this specification illustrate one embodiment of the invention, and together with the description, serve to explain the principles of the invention.

Of the drawings

DESCRIPTION OF THE PREFERRED EMBODIMENT

Reference will now be made in detail to the present preferred embodiment of the invention, an example of which is illustrated in the accompanying drawing.

In accordance with the invention, the multimedication syringe of the present invention is for temporary storage and injection of at least two fluid substances. The syringe comprises a hollow tubular housing having a generally cylindrical wall, an open rear end and a generally tapered partially closed front end defining a discharge passage; a plunger including a portion sized for moving axially within the housing through substantially the entire length thereof, the portion including sealing means surrounding the portion for engaging the inner surface of a housing in a fluid type manner; and resealable port means in the wall of the housing for transmitting fluid into the housing. The plunger is for forcing fluid in the housing out the discharge passage when the plunger is moved axially within the housing from the open end toward the discharge opening.

Figure 1:
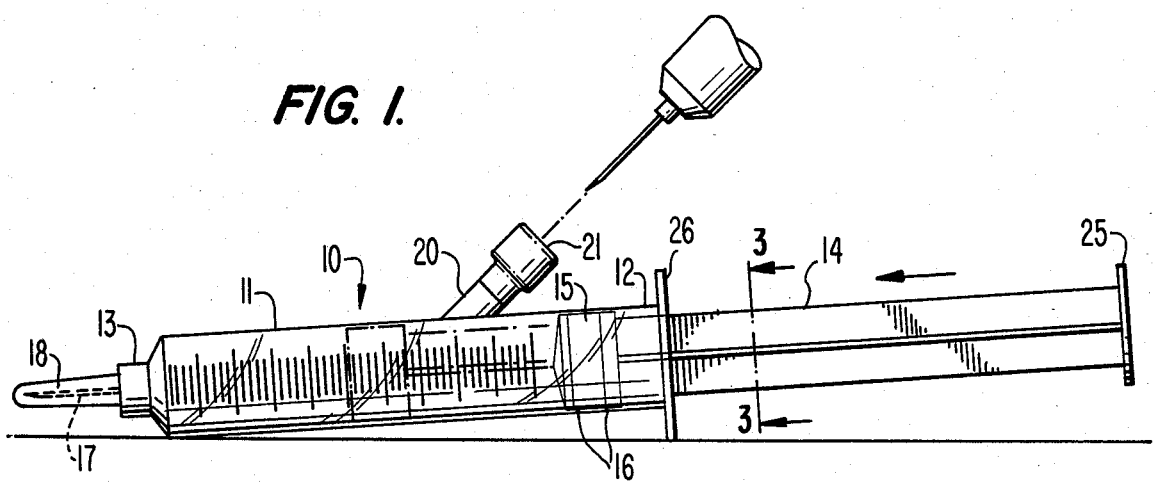
FIG. 1 is a side view of a syringe of the invention supported by the legs.
Figure 2:
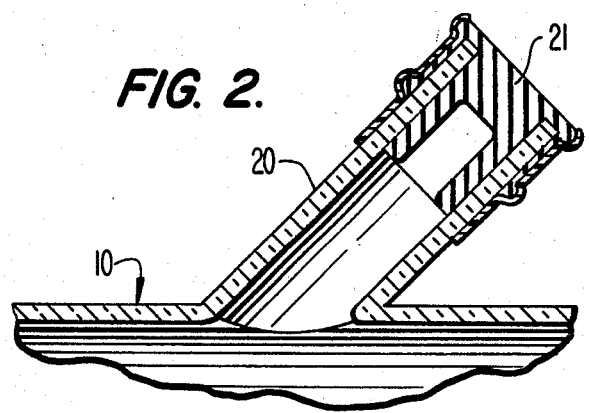
FIG. 2 is an enlarged cross-sectional view of the resealable port of the invention.

As here embodied, and as shown in FIGS. 1 and 2, a hollow tubular housing 10 has a generally cylindrical wall 11 with an open rear end 12 and a generally tapered partially closed front end 13 defining a discharge passage. A plunger 14 includes a portion 15 sized for moving axially within the housing 10 through substantially the entire length thereof. The portion 15 includes sealing means surrounding the portion for engaging the inner surface of the housing in a fluid type manner. As here embodied, the portion 15 comprises a plug, and the sealing means includes ridges 16 thereon engaging the inner surface of the housing. The cylindrical plug may be formed of rubber or other suitable resilient material.

The housing 10 and the plunger 14 are preferably formed of plastic, but glass or other material compatible with the product may be used.

A needle 17 is located in the the discharge passage 13 for injecting the fluid within the syringe into a patient. In addition, a removable cap 18 may be utilized for sealing the discharge passage 13.

As embodied herein, the port means includes a tube 20 having a resilient self-sealing membrane 21 therein. The tube 20 is mounted to the housing 10 for allowing insertion for a syringe needle through the membrane 21, as shown in FIG. 1. The membrane 21 may also be covered with a protective cap (not shown) after the syringe is prepared.

The tube 20 is preferably positioned on the housing 10 for allowing the plug 15 to seal the open end 12 of the housing 10 without interference with fluid transmission through the tube 20.

Figure 3:
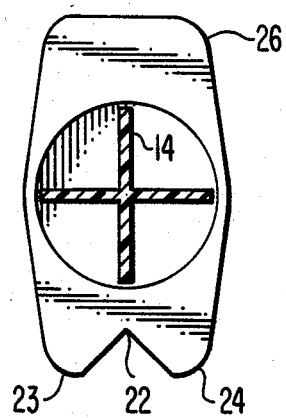
FIG. 3 is a cross-sectional view taken along the line 3—3 of FIG. 1.

As shown in FIG. 3, the housing 10 may also include a groove 22 defining a pair of legs 23 and 24. The legs 23 and 24 allow the syringe to stand on a counter or other surface while receiving the mixture of prescribed injectable medication.

The plunger 14 may also include a flattened end 25 for manually depressing the plunger. The enlarged portion 26 of the housing 10 maybe utilized for holding the syringe with the fingers when the plunger 14 is depressed.

The invention also includes a method of administering multimedication in a single dose without contamination of the supply of the medicines. The method comprises the steps of drawing a first medicine into a first syringe from a supply thereof through the discharge passage of a first syringe; drawing a second medicine from a supply thereof into a second syringe through the discharge passage thereof; injecting the second medicine into the first syringe through a port in the wall of the first syringe; and injecting the multimedication into a patient through the discharge passage of the first syringe.

In addition, if desired the multimedication syringe may simply be loaded with the multiple medications utilizing separate syringes for each medication. In this situation, the syringe is placed on a counter or other surface supported on the legs 23 and 24. Each of the medications is drawn using a separate sterile syringe from a multidose vial, and is injected in turn through the port 20 into the housing 10. The plunger 14 should be drawn to its extreme open position when medications are being transmitted through the port 20. In this position, the plug 15 lies out of the path of any needle inserted through the port 20.

After all the medications are drawn and deposited through the port 20, the multimedication syringe is aspirated of air and the medications are injected into the patient.

Various substances are available for use as a resealable puncturable membrane, as disclosed in the prior art, for example, Sheehan et al. U.S. Pat. No. 4,294,249, which is hereby incorporated by reference.

Thus, it is believed that the present invention provides an efficient and economical means and method for injecting multimedication utilizing multi-dose vials. It will be apparent to those skilled in the art that various modifications and variations could be made in the structure in the invention without departing from the scope or spirit of the invention.

What is claimed is:

1. A multimedication syringe for temporary storage and injection of at least two fluid substances comprising:
   a hollow tubular housing having a cylindrical wall, an open rear end and a tapered partially closed front end defining a discharge passage;
   a plunger including a portion sized for moving axially within said housing through substantially the entire length thereof, said portion including sealing means surrounding said portion for engaging the inner surface of said housing in a fluid-tight manner, said plunger for forcing fluid in said housing out said discharge passage when said plunger is moved axially within said housing from said open end toward said discharge passage; and
   resealable port means in said wall of said housing for transmitting fluid into said housing.

2. The multimedication syringe of claim 1 also including removable means for sealing said discharge passage.

3. The multimedication syringe of claim 2 wherein said removable means includes a cap for tightly surrounding said discharge passage.

4. The multimedication syringe of claim 3 wherein said port means includes a tube having a resilient self-sealing membrane therein, said tube being mounted to said housing for allowing insertion of a syringe needle through said membrane.

5. The multimedication syringe of claim 4 wherein said plunger includes a flattened end for manually depressing said plunger, and said sealing means includes a cylindrical plug having ridges thereon for engaging said inner surface of said housing.

6. The multimedication syringe of claim 5 wherein said plunger includes an enlarged portion having a pair of legs thereon for supporting said syringe on a flat surface.

7. The multimedication syringe of claim 6 wherein said tube is positioned on said housing for allowing said plug to seal the open end of said housing without interference with fluid transmission through said tube.

8. A method of administering medicines in a single dose without contamination of the supplies of said medicines comprising the steps of:

drawing a first medicine into a first syringe from a supply thereof through the discharge passage of said first syringe;

drawing a second medicine from a supply thereof into a second syringe through the discharge passage thereof;

injecting said second medicine into said first syringe through a resealable port in the wall of said first syringe; and injecting said multiple medicines into a patient through the discharge passage of said first syringe.

* * * * *